United States Patent
Deadwyler et al.

(10) Patent No.: US 7,460,904 B2
(45) Date of Patent: Dec. 2, 2008

(54) WIRELESS SYSTEMS AND METHODS FOR THE DETECTION OF NEURAL EVENTS USING ONBOARD PROCESSING

(75) Inventors: Sam A. Deadwyler, Winston-Salem, NC (US); Robert E. Hampson, Kernersville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 588 days.

(21) Appl. No.: 10/682,377

(22) Filed: Oct. 9, 2003

(65) Prior Publication Data

US 2004/0138579 A1    Jul. 15, 2004

Related U.S. Application Data

(60) Provisional application No. 60/417,350, filed on Oct. 9, 2002.

(51) Int. Cl.
*A61B 5/04* (2006.01)
(52) U.S. Cl. .................. 600/544; 600/300; 600/545
(58) Field of Classification Search ................ 600/300, 600/544; 607/45
See application file for complete search history.

(56) References Cited

U.S. PATENT DOCUMENTS

| | | | |
|---|---|---|---|
| 1,662,446 A | 3/1928 | Wappler | |
| 3,421,511 A | 1/1969 | Schwartz et al. | |
| 3,654,933 A | 4/1972 | Hagfors | |
| 5,024,235 A | 6/1991 | Ayers | |
| 5,031,621 A | 7/1991 | Grandjean et al. | |
| 6,016,449 A * | 1/2000 | Fischell et al. | 607/45 |
| 6,155,974 A | 12/2000 | Fish | |
| 6,334,060 B1 | 12/2001 | Sham et al. | |
| 6,366,813 B1 * | 4/2002 | DiLorenzo | 607/45 |
| 6,665,562 B2 * | 12/2003 | Gluckman et al. | 607/2 |
| 2001/0023315 A1 * | 9/2001 | Flach et al. | 600/300 |
| 2001/0029391 A1 * | 10/2001 | Gluckman et al. | 607/2 |
| 2003/0083716 A1 * | 5/2003 | Nicolelis et al. | 607/45 |
| 2003/0083724 A1 * | 5/2003 | Jog et al. | 607/122 |
| 2003/0149457 A1 * | 8/2003 | Tcheng et al. | 607/48 |
| 2003/0195602 A1 * | 10/2003 | Boling | 607/122 |
| 2004/0082875 A1 * | 4/2004 | Donoghue et al. | 600/544 |
| 2005/0090756 A1 * | 4/2005 | Wolf et al. | 600/546 |
| 2006/0293578 A1 * | 12/2006 | Rennaker | 600/378 |

* cited by examiner

*Primary Examiner*—Charles A. Marmor, II
*Assistant Examiner*—Karen E Toth
(74) *Attorney, Agent, or Firm*—Myers Bigel Sibley & Sajovec, P.A.

(57) ABSTRACT

A neural event electrode interface is configured to communicate with electrodes that capture electrical signals that are associated with at least one neuron. A neural event waveform processor is configured to extract neural events from the electrical signals. A wireless transmitter is configured to wirelessly transmit the neural events that are extracted from the electrical signals.

39 Claims, 2 Drawing Sheets

WIRELESS SYSTEMS AND METHODS FOR THE DETECTION OF NEURAL EVENTS USING ONBOARD PROCESSING

CROSS-REFERENCE TO PROVISIONAL APPLICATION

This application claims the benefit of U.S. Provisional Patent Application Ser. No. 60/417,350, filed Oct. 9, 2002, entitled Systems and Methods for Detection of Neural Events, assigned to the assignee of the present application, the disclosure of which is hereby incorporated herein by reference in its entirety as if set forth fully herein.

FEDERALLY SPONSORED RESEARCH

This invention was made with Government support under National Institutes of Health (NIH) Grant Nos. DA 00119, DA 03502, DA 07625, DA 06634, DA 11486, DA 08549 and/or MH 61397 and Defense Advanced Research Projects Agency (DARPA) Contract No. N66001-02-C-8058. The Government has certain rights to this invention.

FIELD OF THE INVENTION

The present invention relates to monitoring and/or recording neurological activity for purposes ranging from research to medicine to robotics.

BACKGROUND OF THE INVENTION

Researchers may desire scientific data relating to neurological activity for many reasons: disease treatments, nerve regeneration, robotics, learning processes, behavioral explanation, direct interfacing between brains and computers, and many other combinations and variations of those endeavors. Current technology in the field includes implanted wire electrodes, connected to field-effect transistors or op-amps that may be connected via small cables to devices that amplify, filter, and analog-to-digital (A/D) convert data, and either provide the complete data stream and store it on a computer or use computer based processors to detect transient events (such as single neuron action potentials), record the detected waveform and time of occurrence, and store the resulting time-stamps on a second computer. The monitored subject is typically tethered to electronic machinery with cables that comprise a number of wires.

Cable tethers of this type may be inhibitive of the behavior patterns in laboratory subjects because they may intrude on the environment by limiting the subject's range of motion and pulling the subject in different directions. Also, the cables sometimes tangle and pull loose implants or electrodes from sensitive areas, which could artificially induce sensations and affect the subjects. When monitoring brain patterns and behavior, unwanted variables (such as sensations, impediments and behavioral adaptations caused by wires) may limit the accuracy of the data.

Prior art systems are embodied and discussed more fully in the following U.S. Pat. No. 1,662,446 to Wappler, U.S. Pat. No. 3,421,511 to Schwartz et al, U.S. Pat. No. 3,654,933 to Hagfors, U.S. Pat. No. 5,024,235 to Ayers, U.S. Pat. No. 6,155,974 to Fish, U.S. Pat. No. 5,031,621 to Grandjean, et al., and U.S. Pat. No. 6,334,060 to Sham, et al.

SUMMARY OF THE INVENTION

Some embodiments of the present invention provide systems and/or methods for detecting neural events using onboard processing. A neural event electrode interface is configured to communicate with electrodes that capture electrical signals that are associated with at least one neuron. A neural event waveform processor is configured to extract neural events from the electrical signals. A wireless transmitter is configured to wirelessly transmit the neural events that are extracted from the electrical signals. By transmitting the extracted neural events rather than the captured electrical signals themselves, according to some embodiments of the present invention, the bandwidth used by each electrode may be reduced, so that more electrodes may be used in a given wireless bandwidth.

In some embodiments of the invention, the neural event waveform processor is configured to extract neural events from the electrical signals by performing time/amplitude window discrimination of the electrical signals. In other embodiments, the neural event waveform processor is configured to extract neural events from the electrical signals by applying template matching to the electrical signals. In still other embodiments, the neural event waveform processor is further configured to time-stamp the neural event, and the wireless transmitter is configured to wirelessly transmit the neural events that are extracted from the electrical signals and the associated time-stamps.

In still other embodiments, the neural event waveform processor is further configured to identify a neuron that is responsible for the neural event, and the wireless transmitter is configured to wirelessly transmit the neural events that are extracted from the electrical signals and the associated identifications of neurons. In still other embodiments, the neural event waveform processor is configured to extract neural events from the electrical signals by detecting occurrence of a neural event in the electrical signals, and by assigning the neural event to a category. The wireless transmitter is configured to wirelessly transmit neural events that are extracted from the electrical signals by transmitting the assigned category.

Other embodiments of the present invention also include a wireless receiver that is configured to wirelessly receive instructions for configuring the neural event waveform processor and to provide the instructions to the neural event waveform processor. In other embodiments, the wireless receiver is configured to wirelessly receive neural stimulation waveforms, and to provide the neural stimulation waveforms to the neural event electrode interface. In yet other embodiments, the neural event waveform processor is further configured to generate neural stimulation waveforms, and to provide the neural stimulation waveforms to the neural event electrode interface.

Some embodiments of the present invention also include a housing. The neural event electrode interface, the neural event waveform processor and the wireless transmitter are contained within and/or on the housing. In some embodiments, the housing is about 5 cubic centimeters in volume.

In some embodiments of the present invention, the neural event waveform processor includes a plurality of amplifiers that are connected to the neural event electrode interface; a plurality of analog-to-digital converters, a respective one of which is responsive to a respective one of the amplifiers; and a digital signal processor that is responsive to the analog-to-digital converters. The wireless transmitter is responsive to the digital signal processor.

In some embodiments, the electrical signals that are associated with at least one neuron are generated by at least one neuron, a collection of neural tissues, brain regions and/or in vitro brain slices. In other embodiments, the electrical signals that are associated with at least one neuron are generated by at least one neuron in conjunction with experimentally relevant externally-applied stimuli; genetic manipulation; before, during and/or after administration of a drug or chemical agent; and/or with a feedback control interface to a prosthesis or other neural interface.

Finally, some embodiments of the present invention also include a base station that is configured to wirelessly receive the neural events that are transmitted by the wireless transmitter and to further process the neural events that are wirelessly transmitted. In some embodiments, the base station is configured to wirelessly receive and process neural events that are transmitted by a plurality of the wireless transmitters.

It will be understood by those having skill in the art that, although the above embodiments have been primarily described with regard to systems for detecting neural events, analogous methods and/or computer program products for detecting neural events also may be provided according to various embodiments of the present invention.

DETAILED DESCRIPTION

Figure 1:
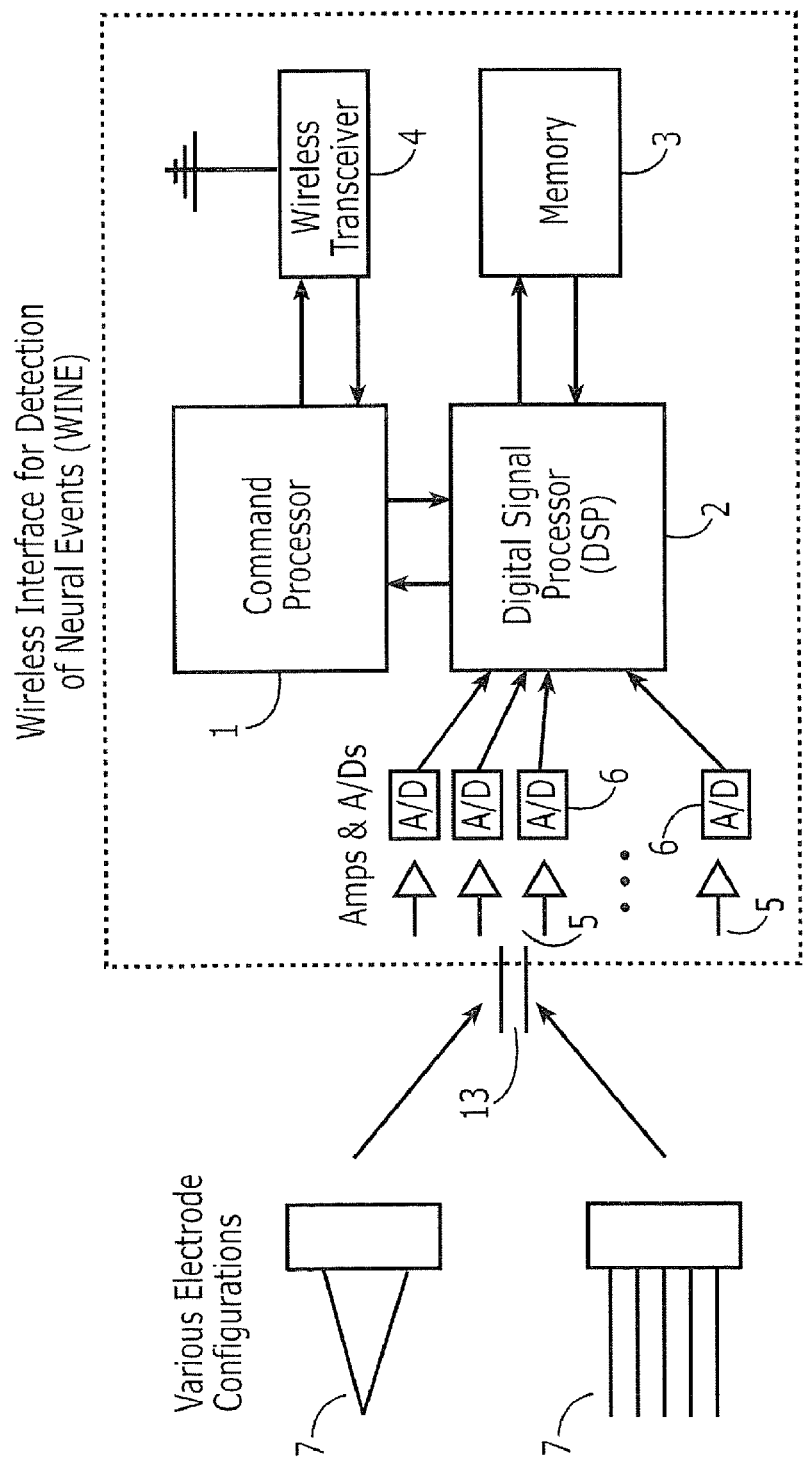
FIG. 1 is a block diagram of an embodiment of the present invention, including amplifiers, analog-to-digital converters, memory, and processors.

The present invention now will be described more fully hereinafter with reference to the accompanying figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The present invention is described below with reference to a block diagram of methods, apparatus (systems) and/or computer program products according to embodiments of the invention. It is understood that a block of the block diagram and combinations of blocks in the block diagram, can be implemented, at least in part, by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagram.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagram.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagram.

As will be appreciated by one of skill in the art, the present invention may be embodied in a method, data processing system and/or computer program product. Thus, the present invention may take the form of an entirely hardware embodiment or an embodiment combining software and hardware aspects.

It should also be noted that in some alternate implementations, the functions/acts noted in the blocks may be combined and/or separated. For example, the functions/acts of two blocks shown may in fact be performed by a single element/step, or the functions/acts of a single block may, in fact, be performed by two elements/steps, depending upon the functionality/acts involved.

Some embodiments of the invention may arise from recognition that wireless technology currently used in neural event monitoring systems typically sends a complete uncompressed data stream from the subject to the processing hardware. This standard telemetry technique may produce systems that may be prohibitive in size and mobility. In other words, the equipment for sending and receiving these uncompressed data streams can weigh heavily on small subjects such as mice and rats, and may inhibit them from behaving naturally, and consequently may contaminate the brain activity that is being monitored. Just as wires may prohibit mobility and affect behavior by acting as a tether in conventional brain-monitoring technology, the size of devices used for wireless communication of other types of data may also impact mobility and behavior because they may be awkward and relatively burdensome on the subject.

Some embodiments of the invention may also arise from recognition that in some conventional systems, multiple subjects may not easily and naturally interact and be recorded in the same closed environment. It may be desirable for subjects to interact with one another while being monitored so that the data reflects neurological activity in a realistic environment. The hardwiring and size of the current technology may prevent the testing of multiple subjects in the same environment because the wires in the tethers may tangle and cross and again affect natural movements and behavior. A related recognition occurs in the testing of in vitro preparations, which may need to be taken out of culture chambers in order to be tested by current systems. It may be advantageous to test samples such as brain slices in a controlled culture environment.

In contrast, some embodiments of the present invention can provide onboard processing for detecting neural events by extracting neural events from the electrical signals that are received from neurons, and then wirelessly transmitting the neural events that are extracted from the electrical signals. By providing onboard processing according to some embodiments of the present invention, efficient use of the wireless bandwidth may be provided, along with relatively small volume systems and/or an ability to simultaneously transmit neural events from multiple neurons and/or subjects.

Certain embodiments of the invention may be referred to as a Wireless Interface for detection of Neural Events (WINE). In one embodiment, a neural analyzer that records multiple discrete neuron signals from brain tissue identifies neuron action potentials, and telemetrically transmits time-stamps with corresponding detected waveforms to a receiver attached to a remote computer for further analysis and storage. Such an embodiment of the invention and other embodiments are described in detail below.

Embodiments of the present invention may provide several potential advantages over existing technology. One potential advantage is that the system/method is wireless and therefore can be less intrusive into the natural environment of the subjects. Another advantage is that the apparatus attached to the subjects can be miniaturized for minimally obtrusive or reduced interference with the subject's activities.

Additionally, in some embodiments, multiple subjects can be monitored in the same "closed" environment without the worries of crossed wires or identifying which data is coming from which subject. Similarly, in some embodiments, subjects can be studied in their own environment, whether that be a culture chamber or other artificially controlled environment or even a completely natural environment.

Figure 2:
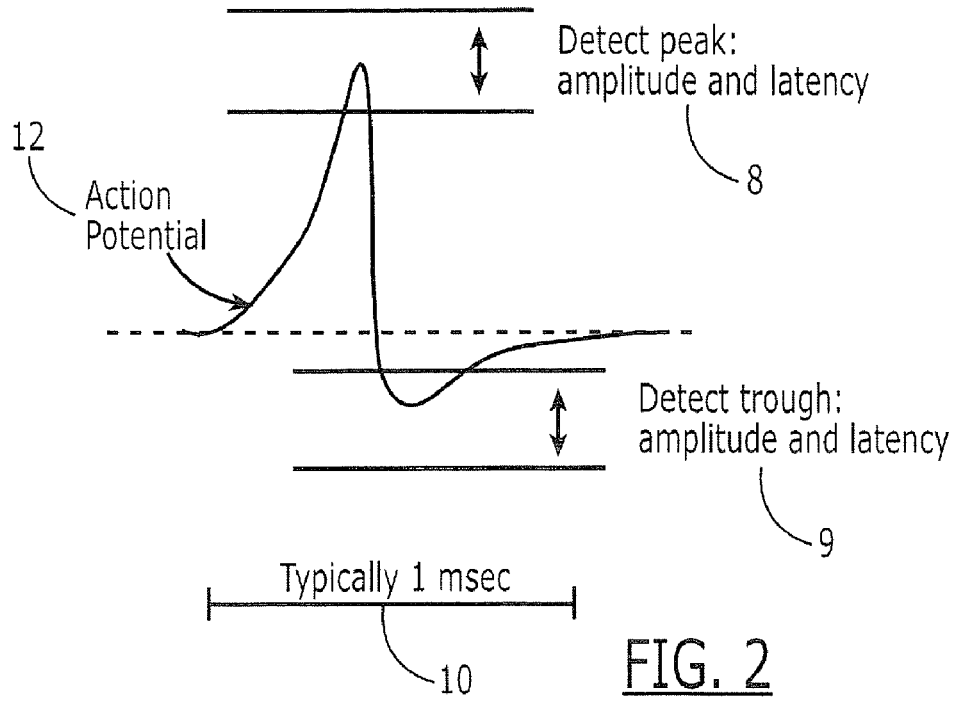
FIG. 2 is a graphical depiction of one type of signal screening that the Digital Signal Processor (DSP) of FIG. 1 and/or other processors may use to select, record, analyze, and transmit neurological data in embodiments of the present invention.
Figure 3:
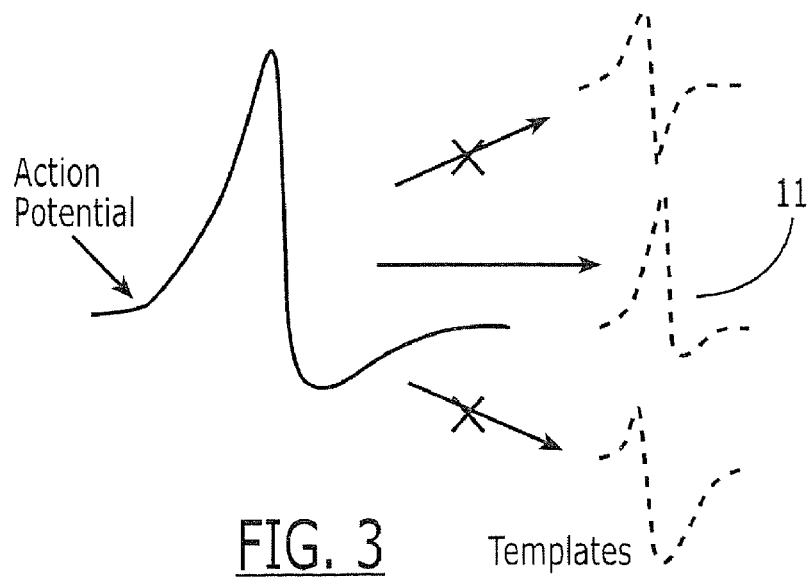
FIG. 3 is another graphical depiction of one type of signal screening that the DSP of FIG. 1 and/or other processors may use to select, record, analyze, and transmit neurophysiological data in embodiments of the present invention.

Embodiments of the present invention are further described below with reference to FIGS. 1, 2, and 3.

With reference to FIG. 1, one embodiment of the present invention is as follows: a system (referred to as "WINE") comprises a command processor 1, a digital signal processor (DSP) 2, memory 3, a wireless transceiver 4 for communicating with other processing units not attached, and a series of amplifiers 5 and analog-to-digital converters 6. WINE also comprises a neural event electrode interface 13 that is able to communicate with different types of electrodes 7. It will be understood that the functionality of devices 1, 2, 3, 5 and/or 6 may provide a neural event waveform processor, which may be embodied in one or more elements. Moreover, in some embodiments, the functionality of devices 1, 2, 3, 5 and/or 6 may not be used in a neural event waveform processor. The functionality of devices 1, 2, 3, 5 and/or 6 may be provided by general purpose hardware, special purpose hardware and/or software.

In some embodiments, multiple electrodes 7 are connected to multiple neurons. For in vivo embodiments, the electrodes 7 can connect to nerve cells in the brain (or slices or cultures of the brain) of the subject and lead outward from the brain to the surface of the subject's head (such as the head of a mouse). The electrodes 7 are connected to the electrode interface 13. The electrodes collect signals (electric impulses) from the nerve cells in the subject's brain and communicate those signals to the WINE through the electrode interface 13. The amplifiers 5 may then amplify the signal from the subject's brain above EEG noise levels. In some embodiments, neural signals may require 5,000× to 10,000× amplification. Neural action potentials are 1,000-10,000 Hz waveforms, yet the slow-wave EEG and noise recorded from the same electrode is 0-500 Hz, thus, in some embodiments, the signals may be filtered to pass >500 Hz.

Next, the analog-to-digital (A/D) converters 6 convert the signal from analog format to a digital format readable by the processing units. A/D conversion may be 12-bit 20-40 kHz resulting in 0.24-0.45 MBPS (megabyte per second) per channel recorded. Once amplified and converted, the signal will pass to the DSP 2 where identified and selected signal types can be time-stamped to indicate time of occurrence, and transmitted via the processor 1 to the wireless transceiver 4. The signals may be selected based on neuron identification criteria communicated to the DSP 2. Examples include time/amplitude window discrimination of waveforms 8, 9 (depicted in FIG. 2) and/or template matching 11 using algorithms for neural event detection (depicted in FIG. 3), or both.

Time-amplitude window discrimination of neuronal action potential signal waveforms can rely on a property of single neurons in that each time a neuron fires, the action potential waveshape is the same, provided that the position of the electrode recording site relative to the neuron also remains the same. Thus, each time a given neuron is active, the recording electrode generally will record the same waveshape. If a different, adjacent neuron is active, the waveshape of the second neuron generally will differ from the first neuron. Thus, in some embodiments, the DSP 2 can monitor and/or record the electrical signal from each recording electrode—when the waveform signal exceeds a set amplitude threshold (i.e., above a background noise level), then 1-3 msec of the succeeding signal can be captured for waveform discrimination. This may take the form of measuring the amplitude of the minimum and maximum waveform amplitude, as well as the time latencies of those points and/or other parameters. Waveforms can thus be sorted into categories based on these measures, and all occurrences of a given waveshape category identified as the "firing" of a corresponding single neuron. Alternatively, waveshapes captured as above can be matched or statistically correlated with predetermined templates (i.e. template matching) to identify single neuron activity. Waveforms can then be categorized statistically by degree of match, or degree of deviation from the template. Thus, all occurrences of a waveform that meet a desired degree of match to the template may be tagged as activity of the single neuron.

The instructions for selecting or discriminating desired signal types may be customized and/or user-written on a computer that then loads instructions to the DSP 2 or can be pre-programmed into the hardware and not customizable. Such instructions could be sent and received via the wireless transceiver 4, such as a radio frequency (RF) antenna. It will be understood by those having skill in the art that when instructions are not wirelessly downloaded to the WINE device of FIG. 1, the wireless transceiver 4 may be configured to include a wireless transmitter for transmitting the processed waveforms.

Once the selected signals are culled (extracted) and time-stamped according to the criteria communicated to the DSP 2, the signal information is transmitted from the WINE Device via the wireless transceiver 4 to a remote processor such as standard personal computers and/or other devices for further processing and analysis. There are several wireless technologies available for radio frequency (RF) transmission—RF devices using the 900 MHz (e.g. cordless phones or cordless keyboards), at 2.4 GHz ("Bluetooth" chips, manufactured by Bluetooth Corp, a division of Ericsson; or IEEE 802.11b standard chips manufactured by Motorola), or at 5.2 GHz (IEEE 802.11a standard chips manufactured by Motorola). Bluetooth and IEEE 802.11b chips are in ready supply, therefore either standard may be applicable to the WINE Device. It will be understood, however, by those having skill in the art, that other conventional wireless transmission techniques may be used. Bluetooth bandwidth is 0.7 MBPS, while IEEE 802.11b is 1-10 MBPS. Given a 20 kHz sampling rate, only about 2-8 channels may be handled if all data is digitized and transmitted. These two wireless telemetry standards support 2-8 channels (uncompressed) of neural recording.

A WINE Device according to some embodiments of the present invention can increase the 2-8 channels to about 16-64 channels. The potentially increased channel capacity may be accomplished by the signal selection described above and depicted in FIGS. 2 and 3, which occurs in the onboard processor on the subject before transmission, making uncompressed telemetering of all data in each channel unnecessary. In other words, only the selected timestamps and waveforms (extracted neural events) may be transmitted by telemetry, which can reduce the bandwidth needed for each channel and make more channels possible. This configuration may differ from a standard device, which may telemeter the entire data stream to an outside processor. It will be understood, however, that in other embodiments, at least some portions of a data stream also may be telemetered unaltered to outside processor.

As has been described, the wireless radio frequency transceiver (RF) 4 may be bi-directional and capable of both sending the neural data to a freestanding processor and receiving instructions regarding how to extract data of a particular type. For instance, it may be desirable for the researcher to be able to change the algorithms and assessment programs implemented by the DSP 2 so that different types of neural activity information can be collected or the same types of information can be collected more accurately—without having to adjust the WINE device by physically disconnecting it from the subject. Further embodiments of the invention include modifications that would allow signal transmissions to stimulate the brain from the operator of the freestanding processor.

In some embodiments of the invention, blocks 1-6 may be contained in and/or on a housing (shown in dashed line in FIG. 1), of approximately 5 cubic centimeters (1.6×1.6×1.6 cm), with a weight that will allow utilization with mice (via head attachment to implanted electrodes for monitoring brain activity) and is capable of transmission of 16-64 channels. Other versions of the device may involve scaling up to 64-128 channels at 15 cubic centimeters (2.2×2.2×2.2 cm) suitable for rats, and up to 256 channels at 40 cubic centimeters (3×3×3 cm) suitable for larger mammals including nonhuman primates and humans.

A WINE Device according to some embodiments of the present invention also may be designed to interface directly with in vitro recording apparatus such as brain-slice chambers utilizing multi-electrode array recording technology and multi-channel EEG recording. A WINE Device may be capable of wireless transmission of 64-256 channels of information from either acute or cultured brain slices, primary cultures of neurons, as well as dissociated adult neurons. The device may allow segregation of signals from individual neurons as specific locations within the culture chamber that correspond to identified synaptic cellular events. Cultured neural networks may also be recordable with a WINE device. As discussed, the recordings can be performed while the in vitro preparations remain in the incubator, allowing it to remain in the controlled culture environment. The WINE Device may allow substantially continual recordings from such in vitro preparations for as long as those preparations are active.

Other embodiments of the present invention are described further below as examples. A non-wireless version of the WINE Device (either alone or in combination with a wireless device) could be utilized in cases where wireless transmission limits the number of subjects or preparations from which recordings could be made. In such cases, it may be possible to disconnect the RF transceiver stage 4 from the signal processing stage 2 (including the on-board processor). Attachment to the device may be implemented via a specialized connector similar to the connection for the RF transceiver stage 4, which could then be attached via cable or fiber optic connection to other data collection devices.

A WINE Device electrode interface 13 according to some embodiments of the invention may be used in two different modes with respect to signals from implanted electrodes. One is via attachment to customized silicon or ceramic probes with pre-determined recording site configuration. In this mode, the device may likely be used in larger mammals where such configured probes can allow high-density recording, but also typically daily placement and removal of the electrode attached to the device. In the second input mode, the WINE Device may mate to standard miniaturized connectors to which wire-recording electrodes (i.e. "tetrodes" or microwire arrays) are attached, primarily for use in mice and other rodents.

In some embodiments, a WINE Device is capable of connecting to Panasonic's MED (Micro-Electrode Dish) system. A WINE device may alternatively be connected to a different in vitro multielectrode culture plate for multiple neurons for recording from brain tissue slices.

In some embodiments, a WINE Device can carry out 2-way communication between the device and the electrode. In such embodiments, the device can be capable of delivering electrical stimulation to any electrode associated with the system while allowing simultaneous recording from other electrodes. In addition, a WINE Device may be capable of stimulation to provide feedback appropriate to analyzed neural events. In some embodiments, such communication is carried out wirelessly.

In other embodiments, a WINE Device may comprise additional processing capability, for example the capability of analyzing neural data on-line with personal computer (PC) interaction. A WINE device may communicate with a processor that analyzes the data and provides on-line reports and data analysis. The reports and data analysis may be accessed locally via the PC, or the reports and data analysis may be recorded on a server and made accessible to the Internet or other computer network.

In addition to the capacity to monitor real-time signals on-line, a WINE Device according to some embodiments of the present invention can form the initial stage of a feedback loop in which the signals that are wirelessly broadcast, analyzed and deciphered to provide information for control of experiments via presentation of both behavioral and physiological stimuli to the same animal or preparation from which the information was originally recorded by the WINE Device. The fact that multiple signals of this number can be discriminated, integrated, and decoded across large populations of neurons can allow development of algorithms capable of time-locking brain activity to behavioral and cognitive outcomes.

Systems and methods for detecting neural events according to embodiments of the present invention can be used for any target subjects. "Subjects", according to the present invention, can be any in vitro or in vivo neuron containing sample or subject whether artificial or natural, and are typically mammalian subjects (e.g., humans, non-human primates, canines, felines, bovines, caprines, ovines, equines, rodents, porcines, and/or lagomorphs). The term "small animals" includes mice, rats, guinea pigs, dogs, cats, monkeys, pigs, and rabbits.

Methods and systems of embodiments of the present invention may be used for drug discovery, drug development, pre-clinical and/or clinical trials, socio and/or behavioral studies, environmental studies, and the like. Particular embodiments may evaluate degenerative brain conditions such as caused by strokes, or diseases such as Alzheimer's, Parkinson's and the like. The evaluations may be used to assess clinical efficacy of a therapy and/or evaluate the disease progression.

The extracted neuron activity data can be obtained in substantially real time via intermittent, episodic, or substantially continuous monitoring during desired monitoring periods to provide information on the biological, physiological, and/or metabolic behavior of a neuron(s) in a brain region(s) of interest. Such data may be employed to assess: (a) single or combination therapies (such as which therapy should precede the other or whether both should be delivered concurrently or proximate to the other, and the like); (b) pharmacokinetics/pharmacodynamics; (c) alterations in or status of neuron activity or function; and (e) drug behavior in drug discovery programs, pre-clinical or clinical trials.

EXAMPLES OF SPECIFIC ANIMAL APPLICATIONS

The following non-limiting examples are provided in further description of the present invention.

Humans/Primates: a WINE Device can be implemented for human and nonhuman primates, which can allow unrestricted movement within enclosed environments (within range of the broadcast of the WINE Device) in order to process large numbers (>100) of neural signals, such as either local or scalp evoked potentials, EEG, or isolated neural events (spikes) from multiple electrode recordings.

Cats, rats, other small animals: a WINE Device would allow true freely-moving behavior coupled with multi-electrode recording.

Mice: a WINE Device may be designed and miniaturized to allow recordings from large numbers of normal and/or genetically altered mice. Such recordings can be obtained within the same housing enclosure for large numbers of instrumented animals utilizing the device to transmit, for example, up to 64 channels of neural information on a 24-hour basis. A WINE Device can allow assessment of alterations in brain activity produced by genetic manipulations (transgenic mice) by comparison of previously described neural correlates, differential sleep patterns such as across a 24-hour period, and/or changes in neural activity related to differences in locomotor patterns (which can also be detected and monitored by a WINE Device). This application includes simultaneous substantially continuous monitoring of multiple animals injected for assessment of drugs with unknown actions on neural activity. Specifically, a WINE Device can be used to instrument animals for assessment of neural toxicity related to long-term exposure to compounds such as drugs and environmental toxins.

A version of a WINE Device with EEG analysis could perform Fourier transform and power spectral analysis (in addition to, or in place of neural waveform detection), which would be a potential advantage for sleep studies.

A version of a WINE Device that interfaces with "Biomimetric" chips capable of mimicking and eventually replacing brain structures could be used for: robotics, prosthetics, or direct brain-computer interfacing, thus possibly applying to human studies.

In the drawings and specification, there have been disclosed embodiments of the invention and, although specific terms are employed, they are used in a generic and descriptive sense only and not for purposes of limitation, the scope of the invention being set forth in the following claims.

What is claimed is:
1. A system for detecting neural events comprising:
a neural event electrode interface that is configured to communicate with electrodes that capture electrical signals that are associated with at least one neuron;
a neural event waveform processor that is configured to extract single neuron action potentials with waveforms that exceed 500 Hz from the electrical signals; and
a wireless transmitter that is configured to wirelessly transmit the single neuron action potentials with waveforms that exceed 500 Hz that are extracted from the electrical signals.
2. A system according to claim 1 wherein the neural event waveform processor is configured to extract the single neuron action potentials with waveforms that exceed 500 Hz from the electrical signals by performing time/amplitude window discrimination of the electrical signals.
3. A system according to claim 1 wherein the neural event waveform processor is configured to extract the single neuron action potentials with waveforms that exceed 500 Hz from the electrical signals by applying template matching to the electrical signals.
4. A system according to claim 1 wherein the neural event waveform processor is further configured to time-stamp the single neuron action potentials with waveforms that exceed 500 Hz and wherein the wireless transmitter is configured to wirelessly transmit the single neuron action potentials with waveforms that exceed 500 Hz that are extracted from the electrical signals and associated time-stamps.
5. A system according to claim 1 wherein the neural event waveform processor is further configured to identify a neuron that is responsible for the single neuron action potentials with waveforms that exceed 500 Hz and wherein the wireless transmitter is configured to wirelessly transmit the single neuron action potentials with waveforms that exceed 500 Hz that are extracted from the electrical signals and the associated neuron identification.
6. A system according to claim 1 wherein the neural event waveform processor is configured to extract the single neuron action potentials with waveforms that exceed 500 Hz from the electrical signals by detecting occurrence of single neuron action potentials with waveforms that exceed 500 Hz in the electrical signals and by assigning the single neuron action potentials with waveforms that exceed 500 Hz to a category, and wherein the wireless transmitter is configured to wirelessly transmit the single neuron action potentials with waveforms that exceed 500 Hz that are extracted from the electrical signals by transmitting the category.
7. A system according to claim 1 further comprising a wireless receiver that is configured to wirelessly receive instructions for configuring the neural event waveform processor to use a selected category of algorithms to extract the single neuron action potentials with waveforms that exceed 500 Hz, and to provide the instructions to use the selected category of algorithms to extract the single neuron action potentials with waveforms that exceed 500 Hz to the neural event waveform processor, wherein the neural event waveform processor is configured to use the selected category of algorithms to extract the single neuron action potentials with waveforms that exceed 500 Hz.
8. A system for detecting neural events comprising:
a neural event electrode interface that is configured to communicate with electrodes that capture electrical signals that are associated with at least one neuron;
a neural event waveform processor that is configured to extract single neuron action potentials with waveforms that exceed 500 Hz from the electrical signals;

a wireless transmitter that is configured to wirelessly transmit the single neuron action potentials with waveforms that exceed 500 Hz that are extracted from the electrical signals; and
a wireless receiver that is configured to wirelessly receive neural stimulation waveforms and to provide the neural stimulation waveforms to the neural event electrode interface, so as to provide the neural stimulation waveforms to the electrodes.

9. A system for detecting neural events comprising:
a neural event electrode interface that is configured to communicate with electrodes that capture electrical signals that are associated with at least one neuron;
a neural event waveform processor that is configured to extract single neuron action potentials with waveforms that exceed 500 Hz from the electrical signals; and
a wireless transmitter that is configured to wirelessly transmit the single neuron action potentials with waveforms that exceed 500 Hz that are extracted from the electrical signals;
wherein the neural event waveform processor is further configured to generate neural stimulation waveforms and to provide the neural stimulation waveforms to the neural event electrode interface, so as to provide the neural stimulation waveforms to the electrodes.

10. A system according to claim 1 further comprising a housing, wherein the neural event electrode interface, the neural event waveform processor and the wireless transmitter are contained within and/or on the housing.

11. A system according to claim 10 wherein the housing is about 5 cubic centimeters in volume.

12. A system according to claim 1 wherein the neural event waveform processor comprises:
a plurality of amplifiers that are connected to the neural event electrode interface;
a plurality of analog to digital converters, a respective one of which is responsive to a respective one of the amplifiers; and
a digital signal processor that is responsive to the analog to digital converters;
wherein the wireless transmitter is responsive to the digital signal processor.

13. A system according to claim 1 wherein the electrical signals that are associated with at least one neuron are generated by at least one neuron, a collection of neural tissues, brain regions and/or in vitro brain slices.

14. A system according to claim 1 wherein the electrical signals that are associated with at least one neuron are generated by an in vitro sample.

15. A system according to claim 1 wherein the electrical signals that are associated with at least one neuron are generated by an in vivo subject.

16. A system according to claim 1 wherein the electrical signals that are associated with at least one neuron are generated by at least one neuron, in conjunction with experimentally relevant externally applied stimuli; in conjunction with genetic manipulation; before, during and/or after administration of a drug or chemical agent; and/or in conjunction with a feedback control interface to a prosthesis or other neural interface.

17. A system according to claim 1 further comprising a base station that is configured to wirelessly receive the single neuron action potentials with waveforms that exceed 500 Hz that are transmitted by the wireless transmitter and to further process the single neuron action potentials with waveforms that exceed 500 Hz that are wirelessly received.

18. A system according to claim 17 further comprising a plurality of neural event waveform processors and wireless transmitters, and wherein the base station is configured to wirelessly receive the single neuron action potentials with waveforms that exceed 500 Hz that are transmitted by a plurality of the wireless transmitters and to further process the single neuron action potentials with waveforms that exceed 500 Hz that are wirelessly received.

19. A method for detecting neural events comprising:
capturing electrical signals that are associated with at least one neuron; then
extracting single neuron action potentials with waveforms that exceed 500 Hz from the electrical signals; and then
wirelessly transmitting the single neuron action potentials with waveforms that exceed 500 Hz that are extracted from the electrical signals.

20. A method according to claim 19 wherein extracting comprises performing time/amplitude window discrimination of the electrical signals.

21. A method according to claim 19 wherein extracting comprises applying template matching to the electrical signals.

22. A method according to claim 19 wherein extracting comprises:
detecting occurrence of single neuron action potentials with waveforms that exceed 500 Hz in the electrical signals; and
assigning the single neuron action potentials with waveforms that exceed 500 Hz to a category; and
wherein wirelessly transmitting comprises wirelessly transmitting the assigned category.

23. A method according to claim 19 further comprising wirelessly receiving instructions to use a selected category of algorithms for extracting single neuron action potentials with waveforms that exceed 500 Hz from the electrical signals.

24. A method according to claim 19 further comprising wirelessly receiving neural stimulation waveforms.

25. A method according to claim 19 wherein the at least one neuron comprises a neuron, a collection of neural tissues, brain areas and/or in vitro brain slices.

26. A method according to claim 19 wherein the at least one neuron comprises an in vitro sample.

27. A method according to claim 19 wherein the at least one neuron comprises an in vivo subject.

28. A method according to claim 19 wherein the electrical signals that are associated with at least one neuron are generated by at least one neuron, in conjunction with experimentally relevant externally applied stimuli; in conjunction with genetic manipulation; before, during and/or after administration of a drug or chemical agent; and/or in conjunction with a feedback control interface to a prosthesis or other neural interface.

29. A method according to claim 19 further comprising:
wirelessly receiving the single neuron action potentials with waveforms that exceed 500 Hz that are wirelessly transmitted; and
further processing the single neuron action potentials with waveforms that exceed 500 Hz that are wirelessly received.

30. A system for detecting neural events comprising:
means for communicating with electrodes that capture electrical signals that are associated with at least one neuron;
means for extracting single neuron action potentials with waveforms that exceed 500 Hz from the electrical signals; and means for wirelessly transmitting the single neuron action potentials with waveforms that exceed 500 Hz that are extracted from the electrical signals.

31. A system according to claim 1 wherein the extracted single neuron action potentials have waveforms that exceed 1000 Hz.

32. A system according to claim 1 wherein the extracted single neuron action potentials have waveforms that exceed 1000 Hz and are less than 10,000 Hz.

33. A system according to claim 1:
wherein the neural event electrode interface is configured to communicate with electrodes that capture electrical signals that are associated with a plurality of neurons; and
wherein the neural event waveform processor is configured to extract a plurality of single neuron action potentials for the plurality of neurons with waveforms that exceed 500 Hz from the electrical signals.

34. A method according to claim 19 wherein the extracted single neuron action potentials have waveforms that exceed 1000 Hz.

35. A method according to claim 19 wherein the extracted single neuron action potentials have waveforms that exceed 1000 Hz and are less than 10,000 Hz.

36. A method according to claim 19:
wherein capturing comprises capturing electrical signals that are associated with a plurality of neurons; and
wherein extracting comprises extracting a plurality of single neuron action potentials for the plurality of neurons with waveforms that exceed 500 Hz from the electrical signals.

37. A system according to claim 8 wherein the wireless receiver is further configured to wirelessly receive instructions for configuring the neural event waveform processor to use a selected category of algorithms to extract the single neuron action potentials with waveforms that exceed 500 Hz, and to provide the instructions to use the selected category of algorithms to extract the single neuron action potentials with waveforms that exceed 500 Hz to the neural event waveform processor, wherein the neural event waveform processor is configured to use the selected category of algorithms to extract the single neuron action potentials with waveforms that exceed 500 Hz.

38. A system according to claim 9 further comprising a wireless receiver that is configured to wirelessly receive instructions for configuring the neural event waveform processor to use a selected category of algorithms to extract the single neuron action potentials with waveforms that exceed 500 Hz, and to provide the instructions to use the selected category of algorithms to extract the single neuron action potentials with waveforms that exceed 500 Hz to the neural event waveform processor, wherein the neural event waveform processor is configured to use the selected category of algorithms to extract the single neuron action potentials with waveforms that exceed 500 Hz.

39. A system according to claim 12 further comprising a wireless receiver that is configured to wirelessly receive instructions for configuring the digital signal processor to use a selected category of algorithms to extract the single neuron action potentials with waveforms that exceed 500 Hz, and to provide the instructions to use the selected category of algorithms to extract the single neuron action potentials with waveforms that exceed 500 Hz to the digital signal processor, wherein the digital signal processor is configured to use the selected category of algorithms to extract the single neuron action potentials with waveforms that exceed 500 Hz.

* * * * *